US00RE48834E

(19) United States
(12) Reissued Patent
Windolf et al.

(10) Patent Number: US RE48,834 E
(45) Date of Reissued Patent: Nov. 30, 2021

(54) METHOD AND A DEVICE FOR COMPUTER ASSISTED SURGERY

(71) Applicant: Synthes GmbH, Zuchwil (CH)

(72) Inventors: Markus Windolf, Davos (CH); Christoph Martin Nötzli, Davos Platz (CH)

(73) Assignee: Synthes GmbH, Zuchwil (CH)

(21) Appl. No.: 16/453,625

(22) Filed: Jun. 26, 2019

Related U.S. Patent Documents

Reissue of:
(64) Patent No.: 9,687,308
Issued: Jun. 27, 2017
Appl. No.: 14/365,633
PCT Filed: Dec. 15, 2011
PCT No.: PCT/CH2011/000299
§ 371 (c)(1),
(2) Date: Jul. 16, 2014
PCT Pub. No.: WO2013/086642
PCT Pub. Date: Jun. 20, 2013

(51) Int. Cl.
*A61B 17/00* (2006.01)
*A61B 34/30* (2016.01)
(Continued)

(52) U.S. Cl.
CPC ..... *A61B 34/30* (2016.02); *A61B 17/1703* (2013.01); *A61B 34/20* (2016.02);
(Continued)

(58) Field of Classification Search
CPC ..... A61B 34/20; A61B 34/30; A61B 34/32; A61B 17/1703; A61B 17/1721;
(Continued)

(56) References Cited

U.S. PATENT DOCUMENTS 5,048,103 A * 9/1991 Leclerc ..... G06K 9/4642 378/98.12
5,368,030 A 11/1994 Zinreich et al.
(Continued)

FOREIGN PATENT DOCUMENTS

EP 1491151 A1 12/2004
WO 03/105659 A2 12/2003
(Continued)

*Primary Examiner* — Robert L Nasser
(74) *Attorney, Agent, or Firm* — BakerHostetler

(57) ABSTRACT

A method for computer assisted determination of values of correction parameters for positioning a medical device relative to a target structure or to a reference base. The method includes a numerical procedure that includes the steps of:

i) automatic detection of the projection of a cylindrical reference means in a medical image and determination of a minimum of four characteristic landmarks within the projection of the cylindrical reference means;
ii) generating a virtual geometric representation of the cylindrical reference means;
iii) determining the virtual projection points representing the characteristic landmarks using a virtual geometric representation of the cylindrical reference means; and
iv) iterative determination of the position and orientation of the cylindrical reference means by matching the virtual projection points of the virtual geometric representation of the cylindrical reference means with the characteristic landmarks of the projection of the cylindrical reference means.

26 Claims, 9 Drawing Sheets

(51) Int. Cl.
*A61B 17/17* (2006.01)
*A61B 34/32* (2016.01)
*A61B 34/20* (2016.01)
*A61B 90/00* (2016.01)

(52) U.S. Cl.
CPC ..... *A61B 34/32* (2016.02); *A61B 90/37* (2016.02); *A61B 90/39* (2016.02); *A61B 17/1721* (2013.01); *A61B 17/1725* (2013.01); *A61B 17/1728* (2013.01); *A61B 17/1753* (2013.01); *A61B 17/1778* (2016.11); *A61B 2017/00818* (2013.01); *A61B 2034/2065* (2016.02); *A61B 2090/376* (2016.02); *A61B 2090/3966* (2016.02)

(58) Field of Classification Search
CPC ..... A61B 17/1725; A61B 17/1728; A61B 17/1753; A61B 17/1778; A61B 2034/2065; A61B 2090/376; A61B 2090/3966
See application file for complete search history.

(56) References Cited

U.S. PATENT DOCUMENTS 6,016,439 A * 1/2000 Acker ..... A61B 5/06 600/411
2001/0044578 A1* 11/2001 Ben-Haim ..... A61B 90/36 600/424
2002/0077540 A1* 6/2002 Kienzle, III ..... A61B 17/1703 600/424
2002/0077543 A1* 6/2002 Grzeszczuk ..... H04N 13/0221 600/424
2004/0186347 A1* 9/2004 Shose ..... A61B 34/20 600/102
2006/0064106 A1 3/2006 Fernandez
2008/0118138 A1* 5/2008 Zingaretti ..... G06T 7/0012 382/132
2008/0234575 A1* 9/2008 Klingenbeck-Regn ..... A61B 6/12 600/431
2009/0054910 A1* 2/2009 Zheng ..... A61B 17/1703 606/130
2011/0028831 A1 2/2011 Kent
2011/0213379 A1 9/2011 Blau et al.
2013/0072784 A1* 3/2013 Velusamy ..... A61B 18/12 600/424

FOREIGN PATENT DOCUMENTS

WO 2003/105659 A2 12/2003
WO 2008/071014 A1 6/2008
WO 2010/025575 * 3/2010 ..... A61B 34/32

* cited by examiner

METHOD AND A DEVICE FOR COMPUTER ASSISTED SURGERY

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

BACKGROUND OF THE INVENTION

1. Field of the Invention

The invention relates to a method for computer assisted determination of positioning parameters for positioning of a medical device relative to a target structure and to a medical device for use with the method.

The task of placing implants plays a key role in trauma and orthopedics as well as in several other medical disciplines. Not only with upcoming minimal invasive techniques, orientation in anatomical terrain is demanding and requires experience of the operator. Prolonged surgery time accompanied by intense radiation and poor surgical results are the consequence. Computer assisted surgery (CAS) concepts aim at easing surgical handling. They are generally based on a three step approach where in a first step medical imaging of the region of interest is required, secondly a virtual surgical plan of the operation is generated and in a third step the surgeon is reliably guided in executing the plan on the patient. Medical imaging is mainly performed by CT (Computed tomography), MRI (Magnetic resonance imaging) or radiography such as 3D isocentric scanning. On the costs of a considerable radiation dose, these technologies deliver highly defined 3D images for convenient planning but confront particularly the smaller clinics with a major investment. Moreover, in many hospitals CT or MRI are considered as a bottleneck in the clinical workflow. After the surgical planning costly and accident-sensitive tracking devices based on optical, mechanical, electromagnetic or acoustic principles are required in the operation room to interlink the patient with the operational plan. This step is called patient registration which is currently one of the most challenging issues in the field of computer aided surgery and influences significantly the overall accuracy of the surgical procedure. For tracking of anatomy and implants, reference bases need to be rigidly and in many cases invasively attached to several relevant elements. This is generally perceived as a time consuming and hindering necessity during surgery. Hence, a simplified assistance technology for reliably and efficiently performing medical interventions carries potential to significantly improve current surgical workflows.

2. Description of the Related Art

A computer assisted surgery system and a method for operating the same is known from US-A 2011/213379 BLAU ET AL. This known computer assisted surgery system essentially comprises a reference body which can be positioned in relation to an anatomical structure, a detector device for detecting the position of the reference body in relation to the anatomical structure and a computer suitably programmed for superimposing the anatomical structure with a virtual representation of a medical device, e.g an intramedullary nail, to modify the position of the reference body and to optimize the virtual position of the medical device, e.g. the intramedullary nail with respect to the anatomical structure.

The reference body can be fixed to a medical tool, e.g. a bore tool or to an intramedullary nail. The reference body is provided with a plurality of fiducial markers which are distributed over the reference body so that the position of the reference body can be determined from a single two-dimensional medical image. Alternatively, the reference body can be a medical tool having a unique geometry to identify the position thereof in a medical image. In another alternative embodiment an intramedullary nail can be the reference body because the intramedullary nail may have a unique form.

The method for operating the above computer assisted surgery system comprises the steps of:

a) positioning of a reference body in relation to an anatomical structure;
b) taking a first 2-dimensional medical image at a first angle, the reference body virtually representing a position of a medical device, e.g. an intramedullary nail to be applied to the anatomical structure;
c) viewing the image data obtained from the first 2-dimensional image on a display device;
d) viewing the anatomical structure with a virtual representation of a medical device, e.g. an intramedullary nail to be applied which is superimposed on the image data;
e) viewing an optimal virtual position of the medical device, e.g. the intramedullary nail to be applied to the anatomical structure so as to obtain a best fit with respect to rules, e.g. a surgical plan for allowable ranges for applying the medical device, e.g. the intramedullary nail to the anatomical structure; and
f) modifying the position of the reference body.

One problem associated with the above described computer assisted surgery system and the method of using the same can be that the position of an implant or a surgical instrument is determined on the basis of a separate reference body comprising a plurality of markers which has to be attached to the implant or instrument in a defined position.

Furthermore, fiducial markers need a comparatively wide spreading for adequate tracking. This can be problematic since the field of view of a conventional C-arm is limited and the space for attachment of the markers is restricted. Furthermore, undesired overlapping in the projected medical image might occur. This wide spreading of the markers or targets is not required when using cylindrical reference means. Radiopaque markers must be embedded into a radiolucent structure like a carbon handle. The fiducial markers cannot be used e.g. on metallic implants. Producing radiolucent means equipped with radiopaque markers is more demanding than drilling holes into existing structures or even using existing holes.

Thus, there remains a need for an improved method and device for computer assisted surgery.

BRIEF SUMMARY OF THE INVENTION

It is an object of the invention to provide a method and a medical device permitting to position the medical device relative to a target structure or to a reference base by means of a computer, wherein the medical device comprises one or more reference means of simple and explicit shape, which are already present in an implant or instrument or which can be easily incorporated in an existing implant or instrument.

The invention solves the posed problem with a method for computer assisted determination of positioning parameters for positioning of a medical device comprising the features as hereinafter disclosed and claimed and with a medical device for use with the method comprising the features as hereinafter disclosed and claimed.

The advantages of the method for computer assisted surgery according to the invention are essentially that:

- the advantage of reference markers realized as cylindrical reference means, e.g. bore holes within radio-opaque material lies in their simplicity. They are easy to produce, can be incorporated in the majority of existing implants and instruments with minimal effort and do not compromise the handling and the surgical workflow. No additional reference objects are needed;
- rapid and robust object tracking is possible by use of simple and explicit-shapes of the cylindrical reference means requiring only a few distinct landmarks in an image for 2D-3D reconstruction;
- already existing holes, e.g. drill guide holes in aiming devices or locking holes in an intramedullary nail can be used as cylindrical reference means;
- the required radiography can be reduced to a minimum of projections;
- orientation of the radiographic device is not critical with the only limitation that a projection of the cylindrical reference means needs to be visible; and
- compared to established surgical practice for routine interventions in a free-hand manner using repeated fluoroscopy, the medical device according to the invention increases surgical precision, reduces operational time and diminishes exposure to radiation of patient and operating room personnel.

Moreover, known surgical navigation systems use position tracking technologies based on optical, electromagnetic or comparable principles. Reference to a targeted anatomical structure needs to be established by a work step called patient registration, interlinking a reference base of the tracking system with a radiographic image or a CT scan. By use of the method and device according to the invention this step can be omitted, since object tracking and registration of anatomical structures are performed by image processing of the same image. A further advantage is essentially to be seen therein that no additional tracking or imaging equipment is needed despite a conventional C-arm which is already available in the majority of clinics. Known surgical workflows can be maintained without additional training or additional qualified staff. Known surgical navigation systems provide real-time tracking of spatial movements of instruments operated in a free-hand manner. The proposed method and medical device provides rigid guiding of instruments or implants in static positions eliminating inaccuracies due to unconstrained manual instrument handling.

As used in this application the term "landmark" has the meaning of a distinctive feature marking a particular location of an object, e.g. detectable anatomical landmarks like a hole, a vertex, an edge or spherical aspects, e.g. a femoral head.

The term "C-arm" includes a medical X-ray image intensifier wherein the C-arm encompasses the X-ray source and an image intensifier, e.g. a fluoroscopic system or an electronic sensor permitting to display and to process the obtained medical image on a computer.

The numerical procedure used to determine the position of the cylindrical reference means with respect to a local system of coordinates generally performs the following steps:

1) detection of all relevant landmarks in the medical image;
2) establishment of a virtual representation of the cylindrical reference means;
3) calculation of virtual projection landmarks depending on the position of the virtual cylindrical reference means; and
4) numerically matching the virtual and actual landmarks by adjusting the virtual position of the medical device to derive the true position with respect to the radiographic device.

Thereby, the position of several objects can be determined in relation to each other and to the anatomy of the patient. Defined surgical manipulation of the positions may then lead to a desired positioning of instruments and/or implants.

After calculation of the actual relative position of all elements, e.g. the medical device and the target structure with respect to each other the situation can be visualized on a display of a computer.

As used herein, the singular form "a", "an" and "the" does not exclude plural references unless the context clearly dictates otherwise. For example, the term "a cylindrical reference means" or "at least one cylindrical reference means" or "a medical image" does not exclude a plurality of cylindrical reference means or a plurality of medical images.

The medical device may be a surgical instrument, e.g. an aiming device or an implant, e.g. an intramedullary nail or a surgical instrument rigidly attached to an implant.

The target structure may be a further surgical instrument or an implant, e.g. an intramedullary nail or an anatomical structure, e.g. a bone comprising characteristic and detectable landmarks like a hole, a vertex, an edge or spherical aspects, e.g. a femoral head.

The reference base may be the operating room, an operating table, a bone or bone fragment, the patient (non-invasive to the skin) or a pre-inserted implant. Generally everything can be used as a reference base which can be maintained in a static position in relation to the target structure or with, depending on the application, acceptable relative movement of the target structure.

An additional medical device may be a screw or a pin or comparable.

Further advantageous embodiments of the method and the device according to the invention can be described as follows.

In a special embodiment the method further comprises before step C) the step of:

B1) detecting at least a portion of an imaged target structure which is received by a projection of the target structure into the medical image by means of the radiographic device.

In a further embodiment of the method the radiographic device has an optical axis and a focal point and the method comprises the additional step of A1) obtaining at least a second medical image of the medical device and of the target structure by means of the radiographic device, wherein the optical axis of the at least one second medical image is adjusted at an angle with respect to its position when obtaining the first medical image.

In a further embodiment the method further comprises the step of A2) determining the position of the local system of coordinates for the at least one second medical image relative to the position of the local system of coordinates for the first medical image.

In another embodiment of the method a 2D-3D reconstruction is obtained from the at least one second medical image and the first medical image.

The spatial position of the medical device relative to the target structure can only be calculated from a single medical image if at least one constrain is known (e.g. the distance between the target structure and the medical device) is known which is the case in e.g. distal locking of an intramedullary nail. If the distance between the target structure and the medical device is not known at least a second medical image from a different view angle is necessary. Assuming that during acquisition of these at least two medical images the cylindrical reference means has not been moved, and both, the cylindrical reference means and the target structure are visible on the medical images the local system of coordinates for the first medical image and the one for the second medical image can be related to each other and the spatial position of the target structure can be obtained.

Preferably, the medical image includes a projection of at least a portion of the medical device including the cylindrical target and of at least a portion of the target structure.

In a further embodiment of the method the medical device is attached to the target structure or to a reference base in a first static position of the medical device relative to the target structure.

Preferably, the numerical procedure comprises the use of a virtual geometric representation of the cylindrical reference means.

In yet another embodiment of the method the cylindrical reference means is in a fixed position relative to the medical device.

In another embodiment of the method the detection of an imaged target structure is performed by using a first set of digital data. The first set of digital data may define a geometric representation or approximation of the target structure or of a specific aspect of the target structure.

In a further embodiment of the method the desired second position of the medical device relative to the target structure and/or the virtual geometric representation of an additional medical device is retrieved from a second set of digital data using the computer. The second set of digital data may be a data set defining a surgical plan or/and a data set defining a desired position of the medical device relative to the target structure only.

In again a further embodiment the method further comprises the step of determining the relation between the position of the local system of coordinates for the at least one second medical image and the position of the local system of coordinates for the first medical image in a global system of coordinates fixed to a set of cylindrical reference means.

In another embodiment of the method the target structure comprises an implant.

In another embodiment of the method the target structure comprises an anatomical structure.

In again another embodiment of the method the target structure comprises an instrument, tool and/or a further medical device comprising a cylindrical reference means.

In a further embodiment of the method the additional medical device comprises an implant, e.g. a bone screw, an instrument, a tool and/or a further medical device.

In a further embodiment of the method further comprising before step A) the step:

positioning of a radiographic device with an optical axis, a focal point and an image sensor with an image field relative to the medical device and the target structure so that at least a portion surrounding the cylindrical reference means of the medical device and a relevant portion of the target structure are projectable into the image field of the image sensor.

In another embodiment of the method the first set of digital data is pre-operatively stored on a data storage of the computer.

In yet another embodiment of the method the second set of digital data is pre-operatively stored on a data storage of the computer. The second set of digital data can comprise a surgical plan of an osteosynthetic or orthopedic treatment including desired relative positions of the medical devices and/or target structures involved in the surgical plan.

In a further embodiment the method additionally comprises the step of transmitting the values of the correction parameters to a robotic positioning device.

In again another embodiment the method comprises the additional step of positioning the medical device in the desired second position relative to the target structure by means of the robotic positioning device.

In another embodiment the method comprises before step A) the steps of:

providing a medical device comprising a cylindrical reference means, wherein the cylindrical reference means has a different density than the surrounding material of the medical device, a longitudinal axis, a height h and a centre; and attaching the medical device to a target structure or to a reference base in a first static position relative to the target structure.

In another embodiment the method further comprises the step of:

planning the desired second position for the medical device relative to the target structure and storing the planned second position as a second set of digital date on the data storage of the computer.

In another embodiment the method comprises the additional step:

displaying the values of the correction parameters between the actual first position and the desired second position of the medical device relative to the target structure on a display of the computer.

In a further embodiment the method comprises the further step of manually positioning the medical device in the desired second position relative to the target structure, preferably by using the displayed values of the correction parameters.

In again a further embodiment the method comprises the further step of positioning the medical device in the desired second position relative to the target structure by using mechanically adjustable devices and by using the displayed values of the correction parameters.

In another embodiment of the method the detection of at least a portion of an imaged target structure which is received by a projection of the target structure into the medical image by means of the radiographic device is automatically performed.

In another embodiment of the method the desired second position of the medial device relative to the target structure and/or the virtual geometric representation of an additional medical device is automatically retrieved from a second set of digital data stored on the data storage of the computer.

In another embodiment of the method the first set of digital data defines a geometric representation or approximation of the target structure or of a specific feature of the target structure.

In a further embodiment of the method the numerical procedure essentially comprises the steps of:

i) automatic detection of a lens-shaped projection of a circular cylindrical reference means in the medical image and determination of the two points of intersection and the first and second apex of the lens-shaped projection of the cylindrical reference means;

ii) generating a virtual geometric representation of the cylindrical reference means with the diameter d, the longitudinal axis, the centre and the height h;

iii) determining the virtual projection points representing the two points of intersection and the first and second apex using the virtual geometric representation of the cylindrical reference means; and iv) iterative determination of the position and orientation of the cylindrical reference means by matching the virtual projection points of the virtual geometric representation of the cylindrical reference means with the two points of intersection and the first and second apex of the lens-shaped projection.

Preferably, the virtual geometric representation includes values for the height h, the diameter d and the position of the centre of the cylindrical reference means.

In another embodiment the device further comprises an attachment means permitting to attach the medical device to a target structure or to a reference base.

In another embodiment of the device the reference base is statically constrained with respect to the target structure.

In another embodiment the device comprises a guiding structure to receive and guide a surgical tool or implant. A surgical tool or implant can be a drill bit, a screw, guide wire, a screw driver, a tap, a scalpel, a cannula or comparable or any other object to be positioned within the patient's body along a specified path.

In again another embodiment of the device the guiding structure is positioned in a fixed position with respect to the cylindrical reference means.

In a further embodiment of the device the guiding structure is positionable in a desired position with respect to the cylindrical reference means.

In another embodiment the device comprises a mechanical means for manually repositioning the medical device relative to the target structure or a reference base with respect to at least one degree of freedom. This mechanical means can be:

- a mechanism for translational and/or rotational adjustment to be operated by a set-screw or a slider from a first state to a second state;
- a flexible and lockable mechanical means like a flexible arm allowing an adjustment with respect to six degrees of freedom and a rigid fixation in a specific position;
- a frictionally engaging connection, e.g. between an intramedullary nail and a bone enabling a maintenance of a static position between two members against external forces while at the same time allowing a manipulation of the position by exceeding the static frictional forces.

In another embodiment of the device the medical device is suitable to receive one or more additional medical devices to match a desired plan without repositioning the medical device itself. For example used for anatomical plating e.g. bone plates, screw lengths and/or screw orientation.

In a further embodiment of the device the actual first position of the medical device is indicated on at least one mechanical or digital scale. For example a mechanical rotational or translational scale attached to the medical device or a scale printed on an adhesive label stuck to the skin of the patient.

In a further embodiment of the device the actual first position of the medical device is transferred to the computer by wire connection or wireless transmission.

In another embodiment of the device the medical device additionally comprises a radiopaque structure visible in X-ray projections. The radiopaque structures can be aligned with virtual geometric representations of the radiopaque structures projected into the X-ray image.

In another embodiment the device comprises computer controlled actuators to position the medical device relative to the target structure in the desired second position.

In again another embodiment of the device the medical device comprises a surgical tool, preferably an aiming device. The aiming device can be attached to a reference base such as an implant, a bone, an operating table or to the skin of the patient or comparable.

In another embodiment the device the medical device comprises an insertion handle attachable to an implant.

In yet another embodiment the medical device comprises an orthopedic or osteosynthetic implant, e.g. an intramedullary nail.

In a further embodiment the medical device comprises a plurality of cylindrical reference means, preferably two or three cylindrical reference means in a known position with respect to each other. In case of circular cylindrical reference means at least a second circular cylindrical reference means is necessary to determine the position of an object with respect to six degrees of freedom. Furthermore, known distances between target centre points can be used to increase the accuracy of determining the position in a direction normal to the projection plane, particularly when using perspective projection.

In a further embodiment of the device all cylindrical reference means are equally sized. Preferably, the longitudinal axes of all cylindrical reference means are parallel. A configuration with equally sized cylindrical reference means and/or an arrangement with parallel longitudinal axes configuration is easy to produce and allows for the largest possible corridor of view angles ensuring that all cylindrical reference means are visible in the medical images.

In another embodiment of the device the longitudinal axes of the cylindrical reference means are arranged at an angle with respect to each other in a defined manner. Preferably, the ratios of the height h to the diameter d of the cylindrical reference means are different. A arrangement of the cylindrical reference means with angled longitudinal axes and/or a configuration of the cylindrical reference means with different ratios h/d allows a unique allocation of each of the cylindrical reference means from its projection and eliminates the risk of numerical procedures converging to local minima and therefore to wrong solutions during iteratively matching virtual and actual projection landmarks.

The device according to the invention is preferably suitable for placement of an intramedullary hip implant.

The device according to the invention can be suitable for anatomical fracture reduction, particularly for adjusting rotational misalignment of fractured long bones.

The device according to the invention can be suitable for distal interlocking of intramedullary nails.

The device according to the invention can be suitable for anatomical plating of a bone, particularly of the proximal humerus.

The device according to the invention can be suitable for insertion of bone screws.

A BRIEF DESCRIPTION OF THE DRAWINGS

Several embodiments of the invention will be described in the following by way of example and with reference to the accompanying drawings in which.

DETAILED DESCRIPTION OF THE INVENTION

Figure 1:
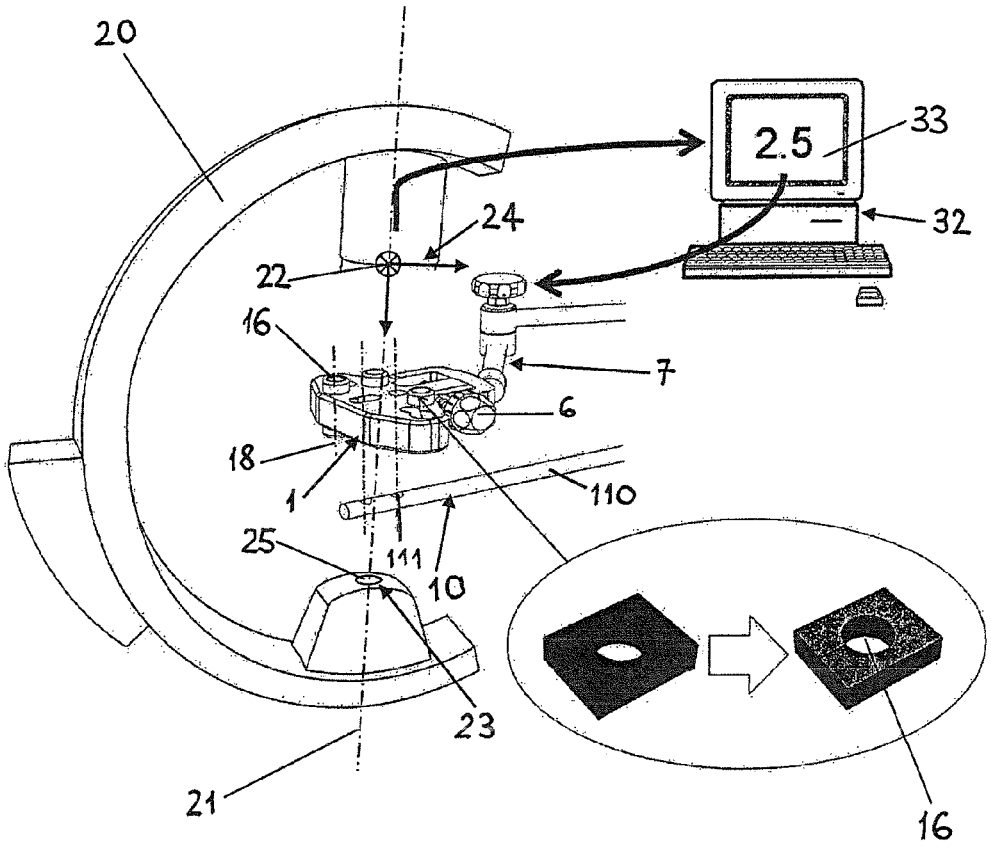
FIG. 1 illustrates a schematic perspective view of an embodiment of the device according to the invention.

Brief Description of the General Clinical Procedure

An implant, e.g. an intramedullary nail 110 and/or instrument equipped with cylindrical reference means 16, e.g. bore holes will be roughly placed with respect to the anatomy of the patient;

The current situation will be statically captured by taking a minimum of one medical image 50 with a conventional radiographic device 20 available in the operation room, e.g. a C-arm. The C-arm can be arbitrarily oriented under the condition that all relevant cylindrical reference means 16 and the relevant anatomy are visible in the medical image 50;

The one or more medical images 50 will then be processed by a specific algorithm including the numerical procedure according to the invention to derive the spatial information of all relevant elements (instruments, implants, anatomy). The algorithm and the numerical procedure can either be implemented on the radiographic device or on an external computer connected to the C-arm. Non-sterile operation room staff, e.g. an X-ray technician can operate the software;

Planning of the desired implant position will be performed on the basis of the taken medical images 50 during the operation. Planning can be performed manually or automatically by image processing algorithms.

The required repositioning of the elements relative to each other will then be calculated;

To reposition and guide the elements according to the plan, the following approaches are possible:

a) Passively guided. The software displays the required correction values on a display unit. The surgeon adjusts a mechanical aiming device accordingly. According to the static nature of the method according to the invention the medical images of the actual situation will be captured, required adjustments will be calculated to match a desired surgical plan; or b) Image guided. The software displays guiding landmarks on the display unit. The surgeon manually matches projections of structures on the instrument or implant with the guiding landmarks under repeated fluoroscopic control; or c) Actively guided. The correction values are sent to a robotic positioning device adjusting the instrument and/or implant automatically. The principle of an actively guided system differs from a passively guided solution therein that actuators automatically perform re-positioning according to the calculated values of the correction parameters. Particularly, in complex applications where several degrees of freedom need to be adjusted, inaccuracy and potential mal-operation by the surgeon may be avoided;

A control image is taken and a control calculation is executed to confirm the desired alignment of the instruments, implants and/or anatomy; and The surgical intervention is subsequently performed by the surgeon.

The processing of the one or more medical images 50 can include:

determining an actual first position of the medical device 1 with respect to a local system of coordinates 24 fixed with the radiographic device 20 by calculating the position of the cylindrical reference means 16 with respect to the local system of coordinates 24 by means of a numerical procedure using a computer 32 and the medical image 50;

detecting at least a portion of an imaged target structure which is received by a projection of the target structure 10 into the medical image 50 by means of the radiographic device 20, wherein the detection of an imaged target structure 10 can be performed by using a first set of digital data. The first set of digital data may define a geometric representation or approximation of the target structure or of a specific aspect of the target structure that can be used as a template. This first set of digital data can be pre-operatively stored on a data storage of the computer 32 permitting to automatically or semi-automatically perform the detection of at least a portion of an imaged target structure; and calculating the actual first position of the medical device 1 relative to the target structure 10 by using the computer 32.

Planning of the desired implant position on the basis of the taken medical images 50 can include the step of retrieving a desired second position of the medical device 1 relative to the target structure 10 and/or retrieving a virtual geometric representation of an additional medical device 3, e.g. bone screw 750 using the computer 32. Thereby, the desired second position of the medical device 1 relative to the target structure 10 and/or the virtual geometric representation of an additional medical device 3 can be retrieved from a second set of digital data using the computer 32. This second set of digital data can be pre-operatively established and stored on a data storage of the computer 32 and can include a surgical plan of an osteosynthetic or orthopedic treatment including desired relative positions of the medical devices 1 and/or target structures 10 and/or a virtual geometric representation of an additional medical device 3 involved in the surgical plan. This allows to retrieve the desired second position of the medial device 1 relative to the target structure 10 automatically or semi-automatically from the second set of digital data stored on the data storage of the computer 32.

The calculation of the required repositioning the elements relative to each other can comprise the step of calculating values of correction parameters between the actual first position and the desired second position of the medical device 1 relative to the target structure 10 and/or values defining a desired position of the additional medical device 3 relative to the medical device 1 by means of the computer 32. After calculation of the actual relative position of all elements with respect to each other the situation can also be visualized on the display 33 of the computer 32 in addition to the correction parameters.

The various steps of the method according to the invention as well as combinations thereof will be described in more detail in the below examples 1 to 5.

Figure 10:
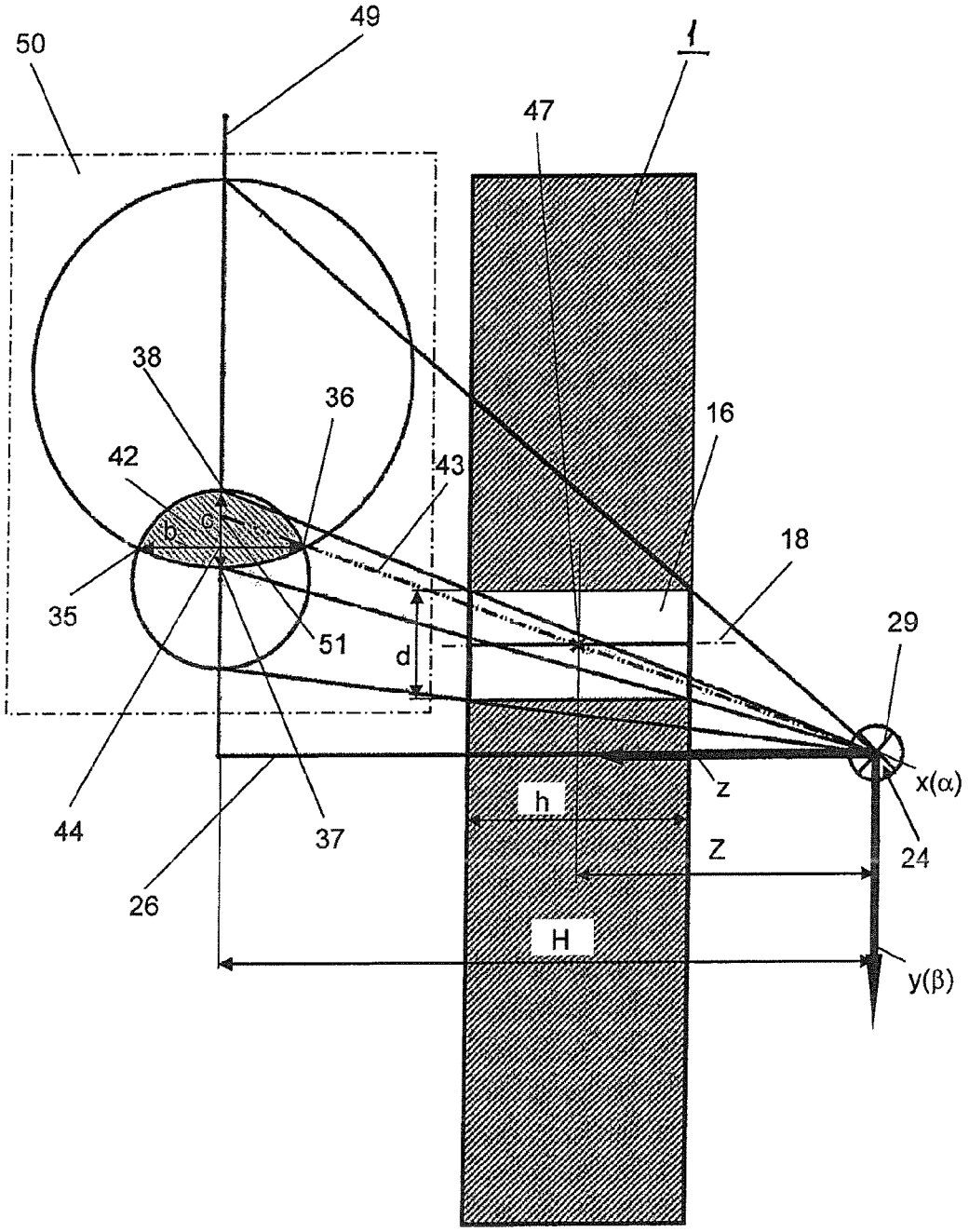
FIG. 10 illustrates a schematic view of a central perspective of a circular cylindrical reference means used in each embodiment of the medical device according to the invention.

FIG. 1 illustrates an embodiment of the device according to the invention including a radiographic device 20, a computer 32 which is electronically connected to the radiographic device 20 and a medical device 1 comprising a cylindrical reference means 16. The computer 32 is programmed to perform the method steps according to the invention. The cylindrical reference means 16 has a different density than the surrounding material of the medical device 1, a longitudinal axis 18, a height h, a diameter d and a centre 47 (FIG. 10). The computer 32 comprises a display 33 permitting to indicate one or more digital scales to display values of correction parameters between the actual first position and the desired second position of the medical device 1 relative to the target structure 10 and/or values defining a desired position of the additional medical device 3 relative to the medical device 1. The medical device 1 can be configured as an aiming device 7 as described below with reference to FIGS. 2 and 3. The target structure 10 comprises an intramedullary nail 110 having a distal end including interlocking holes 111. The radiographic device 20 defines a local system of coordinates 24 and comprises an optical axis 21, a focal point 22 and an image sensor 23 with an image field 25.

Figure 2:
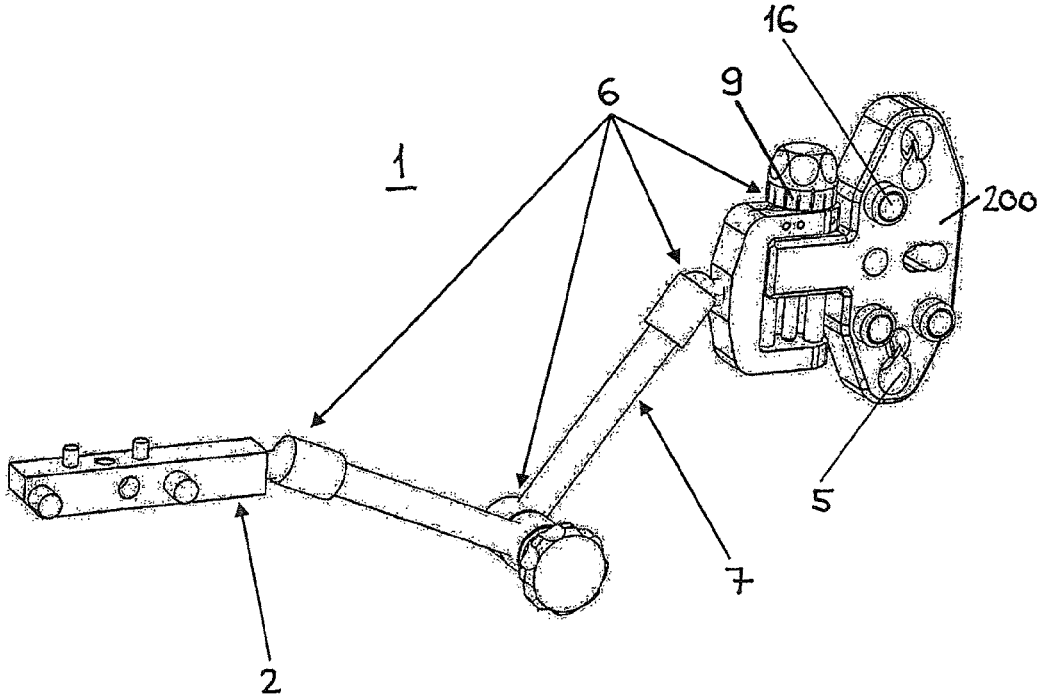
FIG. 2 illustrates a perspective view of a further embodiment of a medical device used with an embodiment of the method according to the invention.
Figure 3:
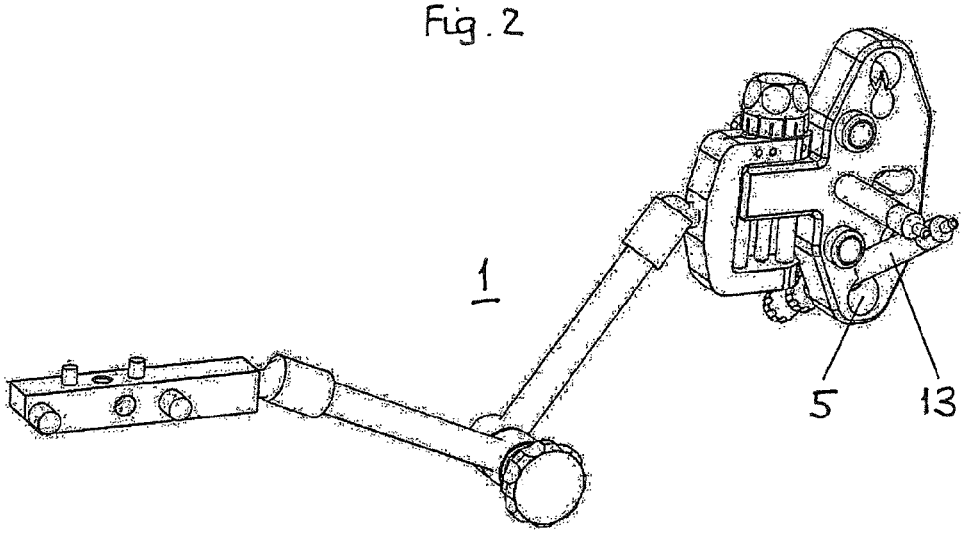
FIG. 3 illustrates a perspective view of the embodiment of a medical device used with the embodiment of the method according to the invention of FIG. 2 with calibration bolts inserted.

In FIGS. 2 and 3 a medical device 1 is illustrated which is configured as an aiming device 7 for use in distal locking of and intramedullary nail 110 (FIG. 1). The medical device 1 essentially comprises a guide body 200 arranged at one end of the medical device 1 which can include three cylindrical reference means 16 and a plurality of guiding structures 5 which can be configured as guide holes penetrating the guide body 200. At the other end of the medical device 1 an attachment means 2 in the form of an adapter is arranged. By means of the attachment means 2 the medical device 1 can be attached to a target structure 10, in particular to an intramedullary nail 110 (FIG. 1) or to a reference base like an operating table. Between the attachment means 2 and the guide body 200 which includes the cylindrical reference means 16 a mechanical means 6 is arranged permitting to manually reposition the guide body 200 of the medical device 1 relative to the intramedullary nail 110 (FIG. 1) which forms the targeting structure 10. The mechanical means 6 comprise a mechanism including a scale 9 for translational adjustment of the guide body 200 and a flexible and lockable arm comprising a plurality of articulations to permit an adjustment of the medical device 1 with respect to six degrees of freedom and a rigid fixation in a desired position. As illustrated in FIG. 3 calibration bolts 13 can be inserted in the guiding structures 5 which permit a pre-calibration to a specific implant such as an intramedullary nail 110 (FIG. 1) before surgery. The guiding structure 5 can be positioned in a fixed position with respect to the cylindrical reference means 16.

Figure 4:
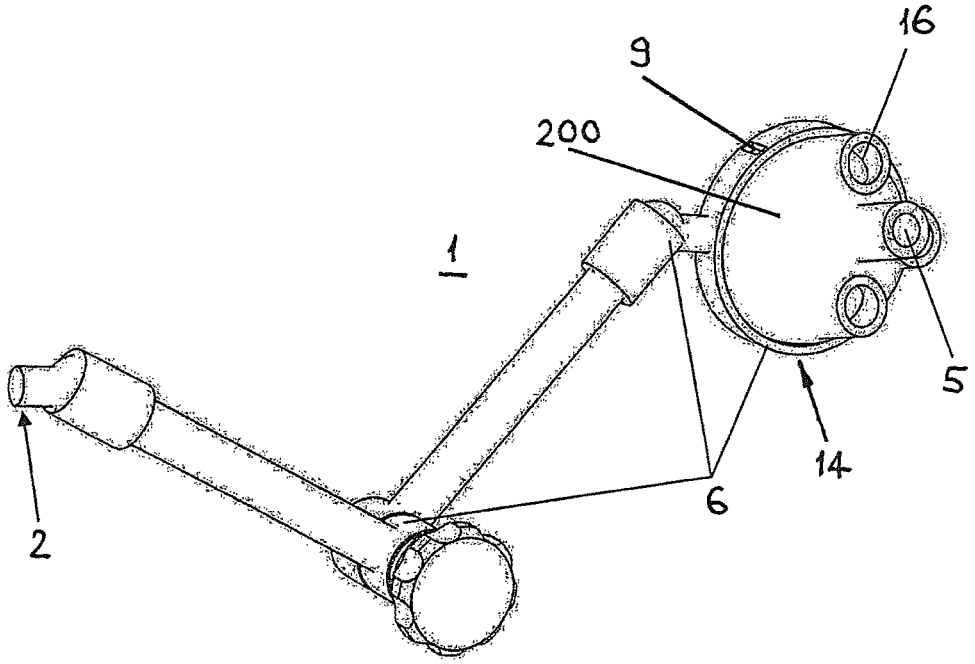
FIG. 4 illustrates a perspective view of a further embodiment of a medical device of FIG. 3 used with various embodiments of the method according to the invention.

FIG. 4 illustrates a medical device 1 for general implant insertion procedures like drilling a hole and screw insertion with respect to an anatomical structure forming the target structure 10 (not shown). The medical device 1 essentially comprises a guide body 200 arranged at one end of the medical device 1 which includes a plurality cylindrical reference means 16 and one or several guiding structures 5 which can be configured as guide holes penetrating the guide body 200. At the other end of the medical device 1 an attachment means 2 in the form of an adapter is arranged. By means of the attachment means 2 the medical device 1 can be attached to a target structure 10 or to a reference base like an operating table. Between the attachment means 2 and the guide body 200 which includes the cylindrical reference means 16 a mechanical means 6 is arranged permitting to manually reposition the guide body 400 of the medical device 1 relative to a targeting structure 10. The mechanical means 6 comprise a mechanism including a scale 9 permitting an adjustment of the guide body 200 with two or three rotational degrees of freedom and a flexible and lockable arm comprising a plurality of articulations to permit an adjustment of the medical device 1 with respect to six degrees of freedom and a rigid fixation in a desired position. The mechanism including the scale 9 can comprise a radiopaque structure 14 in the form of a radiopaque ring or the spherical guide body 200 can be radiopaque permitting to track the translational positioning of the guiding structure 5 relative to a target structure 10 (not shown) by repeated fluoroscopy. Guiding landmarks like a targeting circle (not shown) may be projected into the X-ray image to ease the translational positioning procedure. Alternatively, the medical device 1 can comprise computer controlled actuators to position the medical device 1 relative to the target structure 10 in the desired second position. The position of the medical device 1 can be transferred to the computer by wire connection or wireless transmission.

Figure 5:
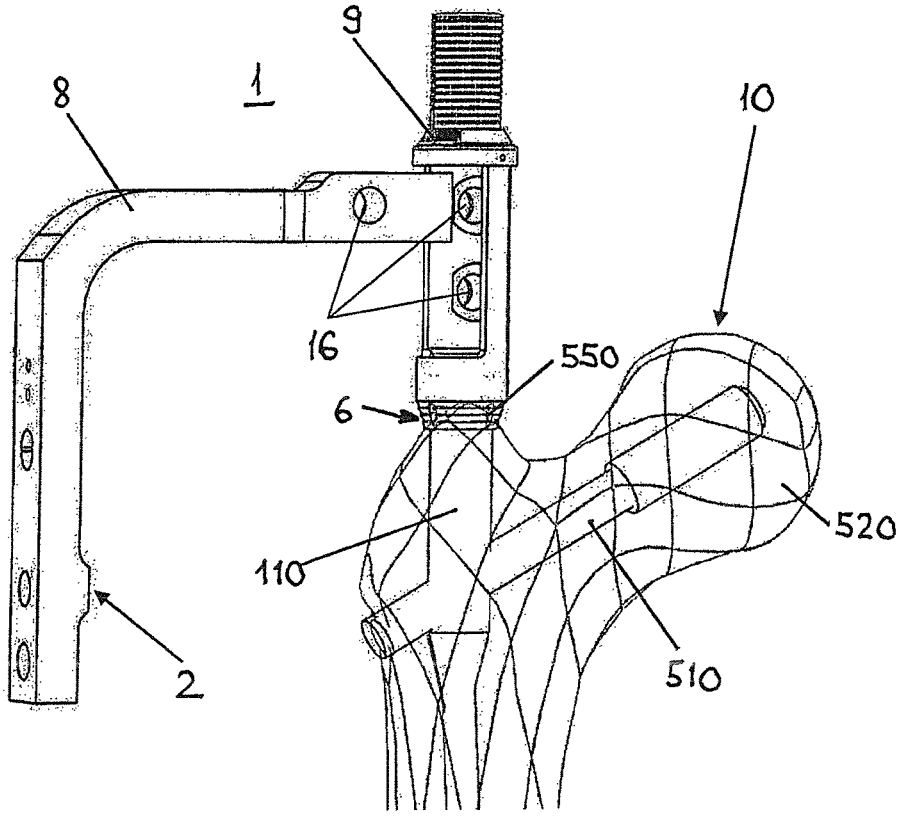
FIG. 5 illustrates a perspective view of another embodiment of a medical device used with an embodiment of the method according to the invention.

FIG. 5 illustrates an embodiment of the medical device 1 for controlled placement of a hip screw 510 or blade into the center of a femoral head 520. Before inserting the hip screw 510 the medical device 1 can be adjusted in two degrees of freedom, namely the insertion depth of the intramedullary nail 110 and the rotation about the axis of the intramedullary nail 110. The medical device 1 can essentially comprise a combination of an insertion handle 8 and an intramedullary hip implant including an intramedullary nail 110 and a hip screw 510. The insertion handle 8 comprises an attachment means 2 at one end permitting an attachment of guiding structures 5 (not shown) and surgical instruments, a plurality of cylindrical reference means 16 and mechanical means 6 permitting to reposition the medical device 1 relative to a target structure 10 formed by the femoral head 520 rotationally and coaxially with respect to the axis of the intramedullary nail 110. The medical device 1 comprises a scale 9 to read the rotational and translational repositioning of the intramedullary nail 110 with respect to the target structure 10. Pins 550 for a temporary fixation of the scale element 9 to the bone are arranged at the terminal end of the mechanical means 6.

Figure 6:
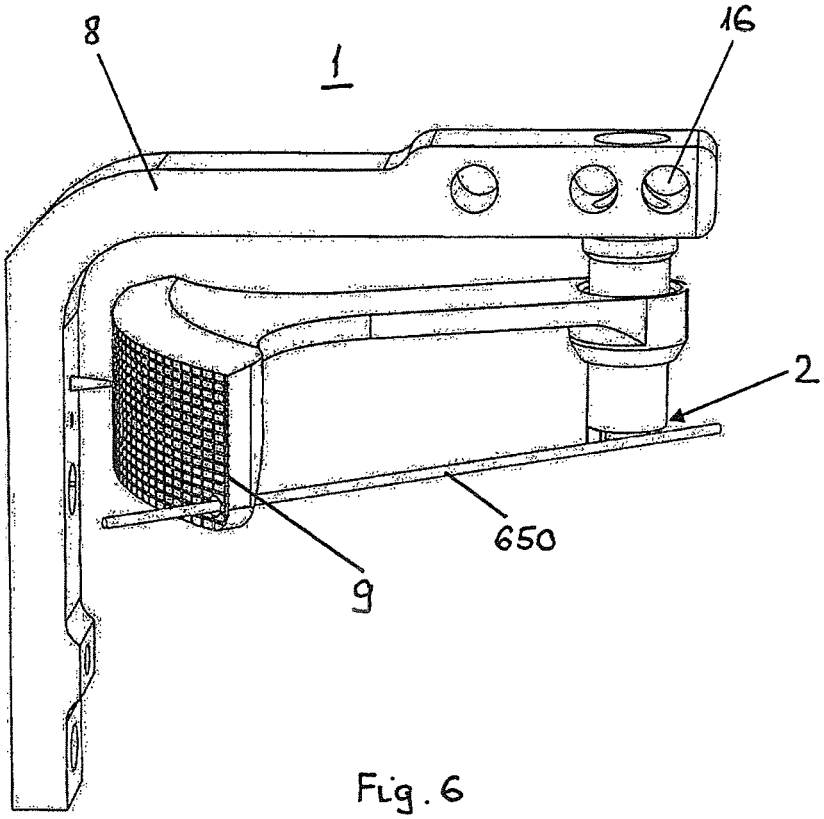
FIG. 6 illustrates a perspective view of again another embodiment of a medical device used with an embodiment of the method according to the invention.

Another embodiment of the medical device 1 for a controlled placement of an intramedullary nail 110 as described with reference to FIG. 5 is illustrated in FIG. 6. The medical device 1 can essentially comprise a combination of an insertion handle 8 and an intramedullary nail 110. The insertion handle 8 comprises an attachment means 2 at one end permitting an attachment of guiding structures 5 (not shown) and surgical instruments, a plurality of cylindrical reference means 16 and mechanical means 6 permitting to reposition the medical device 1 relative to a target structure 10 formed by the femur rotationally and coaxially with respect to the axis of the intramedullary nail 110. The mechanical means 6 comprises a frictionally engaging connection between the intramedullary nail 110 and the target structure 10 formed by the bone (not shown) enabling a maintenance of a static position between the medical device 1 and the target structure 10 against external forces while at the same time permitting a manipulation of the relative position by exceeding the static frictional forces. The scale 9 is attached to the bone to indicate the relative rotational and translational repositioning of the intramedullary nail 11 with respect to the bone. A pin 650 for a temporary fixation of the scale 9 to the bone is attached to the scale 9.

Figure 7:
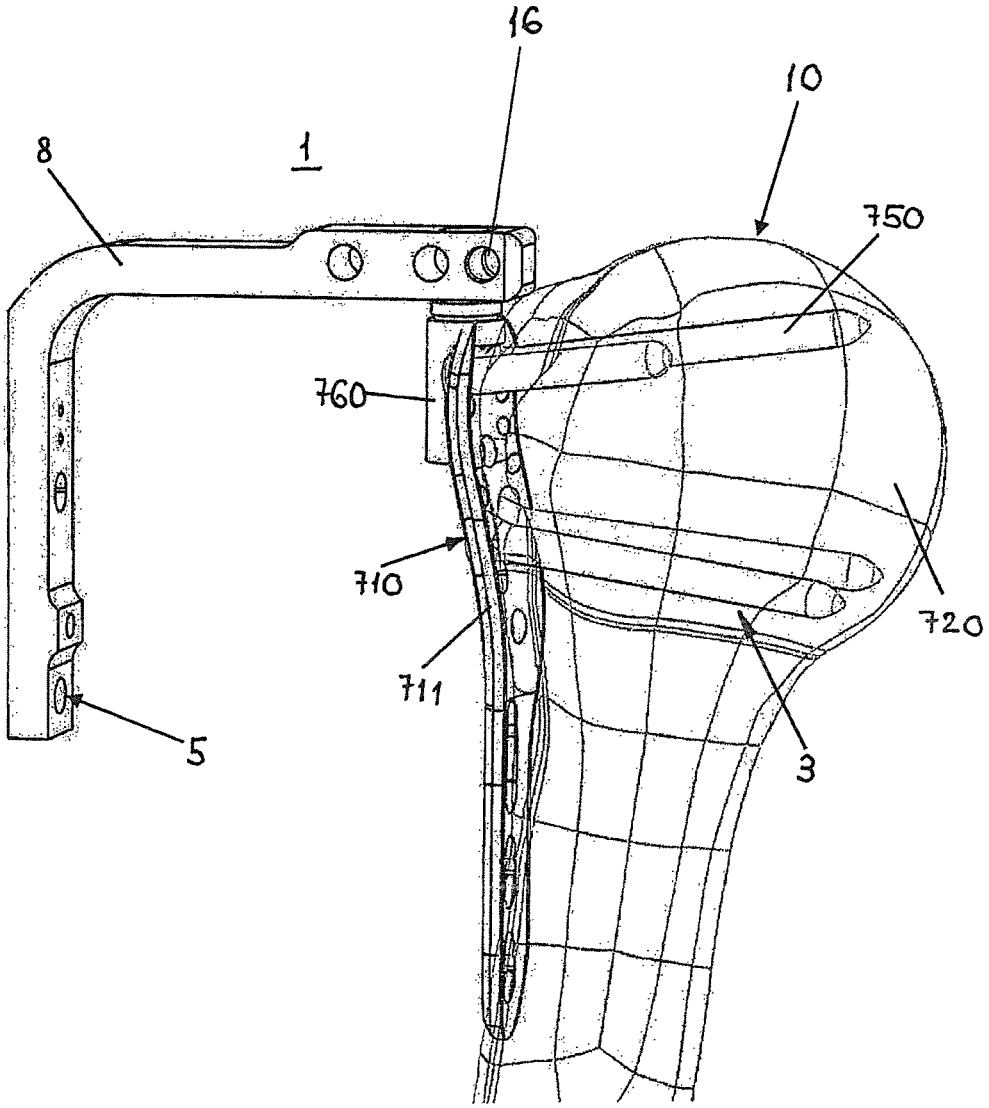
FIG. 7 illustrates a perspective view of yet another embodiment of a medical device used with a further embodiment of the method according to the invention.

FIG. 7 illustrates a further embodiment of the medical device 1 for controlled positioning of a plate implant 710, at the example of a proximal humerus fracture fixation. Ideal screw lengths for angular stable locking bone screws 750 can be determined with respect to the actual position of the medical device 1 relative to the humeral head 720 forming the target structure 10 by using an embodiment of the method according to the invention. The medical device 1 is formed by an insertion handle 8 and a humerus plate 711. The insertion handle 8 comprises a guiding structure 5 for surgical instruments and implants (or permits attachment of a guiding structure 5) at one end, a plurality of cylindrical reference means 16 and a coupling member 760 for coupling the insertion handle 8 to the humerus plate 711. The humeral plate 711 can be temporarily clamped to the humerus to maintain the actual position of the medical device 1 relative to the humeral head 720. The medical device 1 is configured to receive one or more additional medical devices 3 which are configured as bone screws 750. By applying an embodiment of the method according to the invention the screw length of the bone screws 750 can be determined by using values defining a desired position of the additional medical devices 3 relative to the medical device 1, namely the insertion depth of the bone screws 750 calculated by means of the computer 32.

Figure 8:
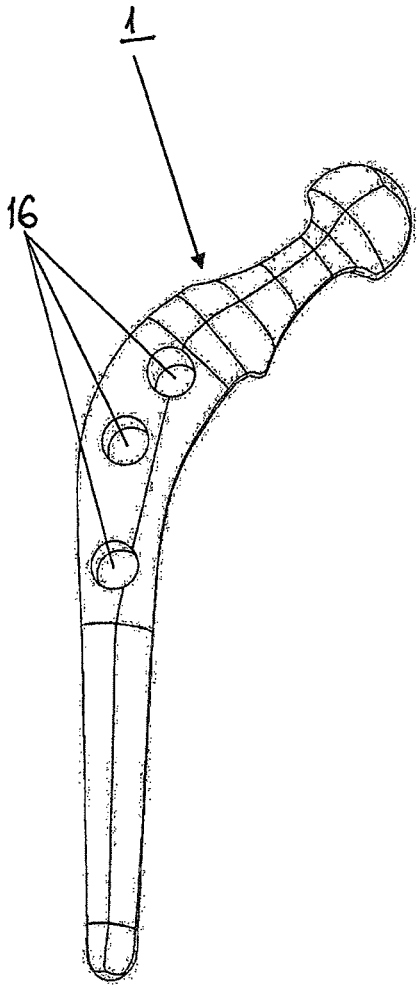
FIG. 8 illustrates a perspective view of again another embodiment of a medical device according to the invention.

FIG. 8 illustrates an embodiment of the medical device 1 consisting of an orthopedic or trauma implant, e.g. a femoral hip implant comprising a plurality of cylindrical reference means 16 for tracking purposes. The position of the medical device 1 relative to a bone or relative to a further medical means such as an acetabular cup forming the target structure 10 can be determined by using the cylindrical reference means 16 of an embodiment of the method according to the invention.

Figure 9A:
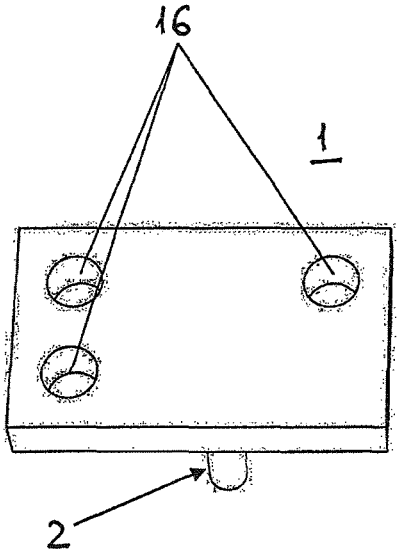
FIGS. 9a and 9b illustrate schematic representations of further embodiments of a medical device according to the invention.
Figure 9B:
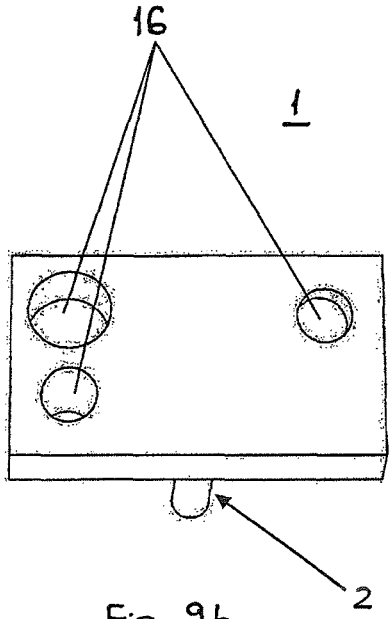

FIG. 9a schematically illustrates a medical device 1 comprising an attachment means 2 for attachment to a target structure 10 (not shown) or to a reference base and three cylindrical reference means 16 which are equally sized and the longitudinal axes 18 of which are parallel. FIG. 9b schematically illustrates a medical device 1 comprising an attachment means 2 for attachment to a target structure 10 (not shown) or to a reference base and three cylindrical reference means 16 the longitudinal axes 18 of which are arranged at an angle with respect to each other in a defined manner and which have different ratios of the height h to the diameter d of the cylindrical reference means 16.

Example 1: Placement of an Intramedullary Hip Implant

Intramedullary hip implants are frequently used for treatment of proximal femur fractures. An intramedullary nail 110 is inserted into the intramedullary channel of the femur and a hip screw 510 or blade is inserted through the intramedullary nail 110 into the femoral head 520 (FIG. 5). Particular in porotic bone, accurate placement of this hip screw 510 is important for stable fixation. To achieve positioning in the center of the femoral head 520, current practice involves repeated radiology in two orthogonal planes. Position of the intramedullary nail 110 can be adjusted in two degrees of freedom, namely the nail insertion depth and the rotation about the nail axis.

To simplify this procedure the medical device 1 according to the invention comprises an implant or a nail insertion handle 8 with cylindrical reference means 16. From two oblique (not necessarily orthogonal) X-ray images displaying the projections of the cylindrical reference means 16 as well as the projection of the femoral head 520 (approximated as perfect sphere) the spatial position of the femoral head 520 is derived with respect to the intramedullary nail 110. Correction values for adjustment of the nail insertion depth and for the nail rotation to achieve a central position of the hip screw 510 inside the femoral head 520 are depicted on a display 33 of a computer 32. In addition the current position of all relevant elements with respect to each other can be visualized on the display 33 as well. A reference scale 9 according FIG. 5 of FIG. 6, showing the actual position of the implant and the performed adjustment of that position, is temporarily attached to the proximal femur 520. After adjusting the implant position according to the values of the correction parameters the standard surgical procedure can be performed.

Example 2: Anatomical Fracture Reduction: Adjusting Leg Rotation

A common complication after intramedullary nailing of a long bone is malrotation of the injured limb. A bone fragment can freely rotate about the axis of an intramedullary nail 110. For the operator it is difficult to define the anatomical orientation of this fragment from a plain X-ray projection.

The method and device according to the invention allow adjusting for example the orientation of a distal femur fragment with respect to the proximal femur fragment before locking the intramedullary nail 110 into place. A medical device 1 according to FIG. 2 without the need for guiding structures 5 or mechanical means 6 is rigidly attached to the insertion handle 8 of a femur intramedullary nail 110 with known orientation between medical device 1 and the intramedullary nail 110. The medical device 1 can be a rigid arm with cylindrical reference means 16 attached to a handle 8. Preferably, a medical device 1 according to FIG. 2 is used because it can be used for distal interlocking of the intramedullary nail 110 as well. Performing the method according to the invention by taking 1 or 2 medical images 50, e.g. X-rays and identifying the posterior-most aspects of the medial and lateral condyles as target structures 10 in the medical images 50 allows calculation of the orientation of the distal femur with respect to the intramedullary nail 110. One medical image 50 is sufficient if assuming a standardized distance between both condyles. Two medical images 50 are required if this distance shall be measured during the procedure. The known orientation of the intramedullary nail 110 with respect to femoral head 520, known for example from proximal locking as described in example 1, allows calculating the current anteversion of the femur. The anteversion can then be corrected by manually rotating the leg of the patient and the procedure can be repeated until a desired anteversion is installed.

Example 3: Distal Interlocking of Intramedullary Nails

Locking an intramedullary nail 110 distally in place is difficult since the intramedullary nail 110 deflects inside the intramedullary channel. The position of the distal interlocking holes 111 (FIG. 1) cannot be predicted from the outside for reliably drilling and inserting the transverse locking bolts.

The method and device according to the invention permits to solve the above problem by use of a medical device 1 according to FIGS. 2 and 3 rigidly attached to an insertion handle 8 of an intramedullary nail 110 analog to example 2. In addition the medical device 1 comprises guiding structures 5 matching with the interlocking pattern of the intramedullary nail 110 to receive and guide a drill-bit and an interlocking bolt. Furthermore, the medical device 1 allows defined mechanical adjustment in two degrees of freedom, namely two translations in a plane normal to the drilling axis or one translation and one rotation about an axis parallel to the drilling axis. Since the distance between the medical device 1 and the intramedullary nail 110 is known, a single medical image 50 is sufficient to calculate the alignment between the interlocking holes 111 and the medical device 1 by automatically identifying the center of the projection of the interlocking hole 111 in the medical image 50 as a target structure 10. Two correction values are calculated by the system according to the installed degrees of freedom on the medical device 1. After executing these corrections drilling and inserting interlocking bolts can be performed.

Opposed to the advantages of simplifying a technically demanding procedure and reducing the required net X-ray exposure to a single X-ray, the disadvantage of this solution can be seen in the fact that it relates to a specific nail family. Several medical devices 1 need to be realized for several nail designs. Another embodiment of the medical device 1 according to the invention targets universal use for a variety of intramedullary nails 110. The medical device 1 comprises instrument guiding structures 5 for various interlocking patterns and allowing adjustment in one translational or rotational degree of freedom transverse to the nail axis in a plane normal to the drilling axis. Furthermore the medical device 1 is configured as an aiming device 7 and comprises as a mechanical means 6 a flexible and lockable arm with an attachment means 2 configured as an adapter section allowing attachment to various nail insertion handles 8. Before an intramedullary nail 110 is inserted into a bone, the medical device 1 is pre-calibrated by attaching it to the insertion handle 8, placing calibration bolts 13 (FIG. 3) with known length through the guiding structures 5 into the corresponding interlocking holes 111, locking the flexible arm in that position and removing the medical device 1 from the intramedullary nail 110. After implantation of the intramedullary nail 110, the medical device 1 is reattached and a single image 50 is acquired and processed according to the method according to the invention. To compensate nail bending inside the intramedullary channel, a single correction value will be calculated and depicted on a display 33 of a computer 32. The medical device 1 will be adjusted accordingly using the mechanical means 6. Afterwards drilling and screw insertion can be safely performed.

The described procedures in examples 1-3 may be combined to assist an entire nailing procedure from a) proximal locking over b) anatomically adjusting the reduction of the fracture to c) distal interlocking. It appears furthermore reasonable to combine steps b) and c). A single medical device 1 and a single medical image 50 displaying the cylindrical reference means 16 of the medical device 1, the interlocking hole(s) 111 of the intramedullary nail 110 and the distal femur condyles is sufficient to define both, anatomical orientation of a distal femur fragment and alignment between drill and the interlocking hole(s) 111.

Example 4: Anatomical Plating of the Proximal Humerus

Particularly for fracture fixation at the proximal humerus accurate placement of fixation elements is of utmost importance. Especially in porotic bone, bone stock is limited and fixation failure is likely to occur. Screws should be placed close to the cortex which carries a risk for penetration of the screws into the articulation.

The method and device according to the invention permits to solve the above mentioned problem by use of a medical device 1 according to FIG. 7 comprising an insertion handle 8 equipped with a plurality of cylindrical reference means 16 and a plate implant 710 rigidly attached to said insertion handle 8. Through a standard surgical approach the plate 711 is positioned with respect to the proximal humerus and temporarily clamped in its current position. From a minimum of two oblique (not necessarily orthogonal) X-ray images displaying the projections of the cylindrical reference means 16 as well as the projection of the humeral head (at least partially approximated as perfect sphere) the spatial position of the humeral head 720 is derived with respect to the plate 711. The number of oblique X-rays may be increased in order to enhance the approximation of the humeral head. Since the positions and directions of the angular stable locking screws 750 to be inserted into the plate body to fix the proximal humerus fragment, are known, penetration points of the screw direction vectors with the approximation of the humeral head can be calculated. Respective screw lengths aiming at approaching the subchondral bone without penetrating into the joint are calculated and depicted on a display. The actual alignment between the elements can be visualized on a display at the same time. The surgeon has the choice to accept the current alignment and screw configuration or may reposition the plate and perform the described procedure again until an acceptable alignment is installed.

Example 6: General Solution for Screw Insertions

A generic approach according to the invention for inserting and using surgical implants and instruments like screws, guide-wires, drill-bits or comparable items along a predefined path inside an anatomical structure is described in the following.

A medical device 1 e.g. according to FIG. 4 is attached to a reference base such as an operation table or a bone part of the patient. A minimum of two oblique (not necessarily orthogonal) X-ray images displaying the projections of the cylindrical reference means 16 attached to the medical device 1 as well as the projection of a targeted anatomical structure, such as the sacroiliac joint in the pelvis or a vertebral body in the spine, are taken. The desired implant or instrument path is manually indicted by the surgeon in all images by digitally placing a line in the X-rays. By use of the method according to the invention the spatial orientation and position of the target path is calculate with respect to the medical device from the images. Translational and/or rotational correction parameters are provided by the system in order to align the guiding structure of the medical device with the desired target path. Translational and rotational degrees of freedom may be realized in various manners, for example the medical device may comprise a sphere as guide body which allows controlled rotational adjustment in two degrees of freedom. Translational adjustment may be performed under repeated fluoroscopy by repositioning the guide body and matching the projection of the guide body with a target circle projected into the X-ray image. The surgical intervention can be performed when alignment between guiding structure and virtual target path is achieved.

FIG. 10 illustrates the steps performed for determining the position of a circular cylindrical reference means 16 in a medical device 1. Said circular cylindrical reference means 16 can be configured as a bore hole so that the cylindrical reference means 16 has a lower density than the surrounding material of the medical device 1. The cylindrical reference means 16 has a longitudinal axis 18, a diameter d, a height h and a centre 47. In particular said steps comprise:

A) acquiring one single medical image 50 (schematically illustrated in the drawing plane of FIG. 6) with a lens-shaped projection 42 of the cylindrical reference means 16 by means of a radiographic device 20 including an ideally punctual energy emitting source 29 with a central ray 26 and a receiving device with an image sensor 23 which is electronically connected to a computer 32 with a display 33. The angulation range between the central ray 26 and the longitudinal axis 18 of cylindrical reference means 16 is restricted in a way that a projection 42 of the cylindrical' reference means 16 must be visible on the medical image 50;

B) determining the position and orientation of the cylindrical reference means 16 from said single medical image 50 using a numerical procedure executed with said computer 32, wherein said numerical procedure essentially comprises the steps of:

a) automatic detection of said lens-shaped projection 42 of said cylindrical reference means 16 in said medical image 50 and determination of the projection points of the two points of intersection 35, 36 and the first and second apex 37, 38 of said lens-shaped projection 42 of said cylindrical reference means 16;

b) generating a virtual geometric representation of said cylindrical reference means 16, with said diameter d, said longitudinal axis 18, said centre 47 and said height h;

c) determining virtual projection points representing said two points of intersection 35, 36 and said first and second apex 37, 38 using said virtual geometric representation of said cylindrical reference means 16 depending on the orientation and position of the virtual geometric representation of the cylindrical reference means 16;

d) iterative determination of the position and angular orientation of said cylindrical reference means 16 by matching said virtual projection points of said virtual geometric representation of said cylindrical reference means 16 with said two points of intersection 35, 36 and said first and second apex 37, 38, wherein said cylindrical reference means 16 has three degrees of freedom:

a position Z on the z-axis of a local system of coordinates 24 measured between the centre of said energy emitting source 29 and said centre 47 of the cylindrical reference means 16. Said virtual geometric representation of said cylindrical reference means 16 can slide along the centre line 43 determined by the centre of projection 44 and the centre of said energy emitting source 29. Said centre of projection 44 is an approximation of the centre-line projection 51 for $h/H \rightarrow 0$. The coordinates x and y of the cylindrical reference means 16 can be uniquely derived for each Z position. Therefore, one cylindrical reference means 16 determines five degrees of freedom but the algorithm needs only three degrees of freedom;

an angle $\alpha$ between said longitudinal axis 18 and said centre line 43 measured in the y-z plane of said local system of coordinates 24 which is fix with respect to the radiographic device 20; and an angle $\beta$ between said longitudinal axis 18 and said centre line 43 measured in the x-z plane of said local system of coordinates 24.

The above mentioned numerical procedure includes a numerical approach for calculating the position of the cylindrical reference means 16 and is based on the following mathematical relationships:

Numerical Approach to Determine the Spatial Position and Orientation of Circular Cylindrical Reference Means:

The procedure relates to the mathematical condition that the projection of the radiographic device 20 is based on an idealized central perspective. A punctiform X-ray source used as energy emitting source 29 sends rays from an origin of known distance H to the projection plane 49.

The procedure incorporates the following fundamental steps:

1. Automatic detection of the lens-shaped projection 42 of said cylindrical reference means 16 in said medical image 50 and determination of significant landmarks, i.e. two points of intersection 35, 36 and the first and second apex 37, 38 of the lens-shaped projection 42 of said cylindrical reference means 16 by use of image processing algorithms. Assumption: With $h/H \rightarrow 0$ the centre-line projection 51 approximates to the centre of projection 44.

2. Simulation of a virtual geometric representation of said cylindrical reference means 16 and of virtual projection points corresponding to the above mentioned landmarks.

3. Iterative optimization of the angular orientation and position of said virtual geometric representation by means of a numerical optimization routine and to determine the actual spatial position and orientation of the cylindrical reference means 16.

It should be understood that if the described procedure is performed on a single circular cylindrical reference means 16, five degrees of freedom can be obtained, since the cylindrical target 16 is rotation symmetric. Using two or more cylindrical reference means 16 allows constraining an object in 6 degrees of freedom.

Iterative Determination of the Orientation of the Cylindrical Reference Means or of a Set of Cylindrical Reference Means A virtual geometric representation of said cylindrical reference means 16 is generated with the known attributes d (diameter) and h (length). The virtual geometric representation of said cylindrical reference means 16 has one translational degree of freedom. It can slide along the central line 43, determined by the centre of projection 44 and the centre of said energy emitting source 29. Sliding position is controlled by Z (FIG. 10). With further two rotational degrees of freedom ($\alpha$, $\beta$) the position of said virtual geometric representation of said cylindrical reference means 16 is fully constrained.

Four virtual projection points representing said two points of intersection 35, 36 and said first and second apex 37, 38 are derived from the orientation of said virtual geometric representation of said cylindrical reference means 16.

A numerical optimization routine is used to find a global minimum for the deviations between said significant landmarks the actual projection points and the corresponding virtual projection points using three degrees of freedom (DOF) ($\alpha$, $\beta$, Z) in order to carry out the optimized orientation of said virtual geometric representation of said cylindrical reference means 16. Due to the asymmetry of the lens-shaped projection 42 (segments b and c appear asymmetrically, due to the nature of a central projection) it is possible to calculate a unique solution for the orientation of the cylindrical reference means 16 from a single image.

The procedure can be extended by use of a plurality of circular cylindrical reference means 16 with known distances and alignment to each other. The entirety of all deviations between virtual and actual projection landmarks of all cylindrical reference means 16 is numerically minimized over said three degrees of freedom. This approach has the following advantages:

a) the position of an object comprising a set of circular cylindrical reference means 16 (at least two) can be tracked in 6 degrees of freedom and is thereby fully constrained.

b) Taking distances between centre points 47 of cylindrical reference means 16 into account increases the accuracy of determining the Z-dimension.

c) With additional redundant landmarks in the equation, the accuracy of the procedure increases and the risk of the algorithm converging to wrong solutions (local minima) decreases.

Numerical Procedure to Determine the Spatial Position of an Unconstrained Target Structure from Two Oblique Projections with Respect to a Set of Cylindrical Reference Means When aiming at reconstructing the position in space of a significant landmark within an X-ray projection, such as a vertex or edge of a bone or the centre of a femoral/humeral head, the previously described procedure can be used in the following way:

1. Acquiring two oblique medical images 50 of the target structure 10 and of a set of cylindrical reference means 16 under the precondition that target structure 10 and cylindrical reference means 16 remain at a static position during imaging.
2. Detecting a significant landmark of the target structure 10 and the projection of the set of cylindrical reference means 16 in both medical images 50.
3. Determining the spatial position and orientation of the set of cylindrical reference means 16 in both medical images 50 in coordinates of a local coordinate system 24 (COS) rigidly bonded with the radiographic device 20 by using the previously described procedure.
4. Determining the relation between both local COS in a global set of coordinates rigidly bonded with the set of cylindrical reference means 16.
5. Transforming the line determined by the projected landmark of the target structure 10 to the centre of the energy emitting source of the radiographic device 20 into the global system of coordinates for both medical images 50.
6. The point of intersection of both lines defines the spatial position of the landmark of the target structure 10 with respect to the set of cylindrical reference means 16.

It should be understood that the procedure can be extended by increasing the number of oblique projections. More images allow more accurate 2D-3D conversion of more complex geometrical structures. However, this increases at the same time the complexity of the procedure and the radiation exposure to the operator, to the operating room personnel and to the patient.

While various descriptions of the present invention are described above, it should be understood that the various features can be used singly or in any combination thereof. The scope of the present invention is accordingly defined as set forth in the appended claims.

The invention claimed is:

1. A method for computer assisted determination of values of correction parameters for positioning a medical device in spatial relation to a target structure comprising the steps of:

A) obtaining a medical image of the medical device and the target structure [by means of] *using* a radiographic device, wherein the medical device comprises a cylindrical reference means that is surrounded by material of the medical device, and wherein the cylindrical reference means has a different density than the surrounding material of the medical device;

B) determining an actual first position of the medical device with respect to a local system of coordinates fixed with respect to the radiographic device by calculating a position of the cylindrical reference means with respect to the local system of coordinates [by means of] *using* a numerical procedure using a computer and the medical image;

C) calculating an actual first position of the target structure in spatial relation to the medical device by using the computer;

D) retrieving a desired second position of the medical device in spatial relation to the target structure;

E) calculating values of one or more correction parameters between the actual first position and the desired second position of the medical device in spatial relation to the target structure [by means of] *using* the computer; and F) positioning the medical device in the desired second position in spatial relation to the target structure using the values of one or more correction parameters calculated in step E);

wherein the numerical procedure comprises the steps of:

[i) automatically detecting a projection of the cylindrical reference means in the medical image and determining a minimum of four characteristic landmarks within the projection of the cylindrical reference means;

ii) generating a virtual geometric representation of the cylindrical reference means;

iii) determining virtual projection points representing said characteristic landmarks using the virtual geometric representation of the cylindrical reference means; and iv) iteratively determining the position and orientation of the cylindrical reference means by matching the virtual projection points of the virtual geometric representation of the cylindrical reference means with the minimum of four characteristic landmarks within the projection of the cylindrical reference means]

[v)] *i)* automatically detecting a lens-shaped projection of the cylindrical reference means in the medical image and determining two points of intersection and [the ] a first and second apex of the lens-shaped projection of the cylindrical reference means;

[vi)] *ii)* generating [the] *a* virtual geometric representation of the cylindrical reference means with the diameter d, the longitudinal axis, the center and the height h;

[vii)] *iii)* determining [the] virtual projection points representing the two points of intersection and the first and second apex using the virtual geometric representation of the cylindrical reference means; and

[viii) iteratively] *iv*) determining the position and orientation of the cylindrical reference means by matching the virtual projection points of the virtual geometric representation of the cylindrical reference means with the two points of intersection and the first and second apex of the lens-shaped projection;

and additionally comprising the step of transmitting the values of the correction parameters to a robotic positioning device, wherein the positioning of the medical device in the desired second position relative in spatial relation to the target structure is effectuated [by means of] *using* the robotic positioning device.

2. The method according to claim 1, further comprising before step C) the step of:

B1) detecting at least a portion of an imaged target structure which is received by a projection of the target structure into the medical image [by means of] *using* the radiographic device.

3. The method according to claim 1, wherein the radiographic device has an optical axis and a focal point and the method comprises before step B) the additional step of:

A1) obtaining at least a second medical image of the medical device and of the target structure [by means of] *using* the radiographic device, wherein the optical axis of the radiographic device when obtaining the at least one second medical image is adjusted at an angle with respect to its position when obtaining the first medical image.

4. The method according to claim 3, further comprising the step of:

A2) determining a position of the local system of coordinates for the at least one second medical image in spatial relation to the position of the local system of coordinates for the first medical image.

5. The method according to claim 3, further comprising generating a 2D or 3D reconstruction based on information obtained from the at least one second medical image and the first medical image.

6. The method according to claim 1, wherein the medical image includes a projection of at least a portion of the medical device including the *lens shaped projection of the* cylindrical reference means and of at least a portion of the target structure.

7. The method according to claim 1, wherein the medical device is attached to the target structure in a first static position.

8. The method according to claim 1, wherein the cylindrical reference means is fixed to the medical device.

9. The method according to claim 2, wherein the detection of an imaged target structure is performed by using a first set of digital data.

10. The method according to claim [1] *9*, wherein under step D) the desired second position of the medical device relative to the target structure is retrieved from a second set of digital data using the computer.

11. The method according to claim 3, further comprising the step of determining the relation between the position of the local system of coordinates for the at least one second medical image and the position of the local system of coordinates for the first medical image in a global system of coordinates fixed to a set of cylindrical reference means.

12. The method according to claim 1, wherein the target structure comprises an implant.

13. The method according to claim 1, wherein the target structure comprises an anatomical structure.

14. The method according to claim 1, wherein the target structure comprises one or more of an instrument, a tool and a further medical device comprising a cylindrical reference means.

15. The method according to claim 1, further comprising before step A) the step:

positioning of a radiographic device with an optical axis, a focal point and an image sensor with an image field in spatial relation to the medical device and the target structure so that at least a portion surrounding the cylindrical reference means of the medical device and a relevant portion of the target structure are projectable into the image field of the image sensor.

16. The method according to claim 9, wherein the first set of digital data is pre-operatively stored on a data storage of the computer.

17. The method according to claim 10, wherein the second set of digital data is pre-operatively stored on a data storage of the computer.

18. The method according to claim 1, comprising before step A) the steps of:

providing the medical device comprising the cylindrical reference means, wherein the cylindrical reference means has a longitudinal axis, a height h and a center; and attaching the medical device to the target structure in a first static position.

19. The method according to claim 1, further comprising before step D) the step of:

planning the desired second position for the medical device in spatial relation to the target structure and storing the planned second position as a second set of digital data on a data storage of the computer.

20. [The method according to claim 1, comprising the additional step:

G) displaying the values of the correction parameters between the actual first position and the desired second position of the medical device in spatial relation to the target structure on a display of the computer.] *A method for computer assisted determination of values of correction parameters for positioning a medical device in spatial relation to a target structure comprising the steps of:*

*A) obtaining a medical image of the medical device and the target structure using a radiographic device, wherein the medical device comprises a cylindrical reference means that is surrounded by material of the medical device, and wherein the cylindrical reference means has a different density than the surrounding material of the medical device;*

*B) determining an actual first position of the medical device with respect to a local system of coordinates fixed with respect to the radiographic device by calculating a position of the cylindrical reference means with respect to the local system of coordinates using a numerical procedure using a computer and the medical image;*

*C) calculating an actual first position of the target structure in spatial relation to the medical device by using the computer;*

*D) retrieving a desired second position of the medical device in spatial relation to the target structure;*

*E) calculating values of one or more correction parameters between the actual first position and the desired second position of the medical device in spatial relation to the target structure using the computer; and*

*F) positioning the medical device in the desired second position in spatial relation to the target structure using the values of one or more correction parameters calculated in step E);*

*wherein the numerical procedure comprises the steps of:*

*i) automatically detecting a lens-shaped projection of the cylindrical reference means in the medical image and determining two points of intersection and a first and second apex of the lens-shaped projection of the cylindrical reference means;*

*ii) generating a virtual geometric representation of the cylindrical reference means with the diameter d, the longitudinal axis, the center and the height h;*

*iii) determining virtual projection points representing the two points of intersection and the first and second apex using the virtual geometric representation of the cylindrical reference means; and*

*iv) determining the position and an orientation of the cylindrical reference means by matching the virtual projection points of the virtual geometric representation of the cylindrical reference means with the two points of intersection and the first and second apex of the lens-shaped projection; and*

*G) displaying the values of the correction parameters between the actual first position and the desired second position of the medical device in spatial relation to the target structure on a display of the computer.*

21. The method according to claim [1] *20*, wherein the [step of positioning] medical device *is manually positioned* in the desired second position in spatial relation to the target structure [is performed manually].

22. The method according to claim 20, wherein the step of positioning the medical device in the desired second position in spatial relation to the target structure is performed using mechanically adjustable devices and by using the displayed values of the correction parameters.

23. The method according to claim [1] *2*, wherein the detection of at least a portion of an imaged target structure which is received by a projection of the target structure into the medical image [by means of] *using* the radiographic device in step C) is automatically performed.

24. The method according to claim [1] *9*, wherein the desired second position of the medical device in spatial relation to the target structure is automatically retrieved from a second set of digital data stored on the data storage of the computer.

25. The method according to claim 9, wherein the first set of digital data defines a geometric representation or approximation of the target structure or of a specific feature of the target structure.

26. The method according to claim 1, wherein the virtual geometric representation includes values for the height h, the diameter d and the position of the center of the cylindrical reference means.

* * * * *